(12) United States Patent
Cardinale

(10) Patent No.: US 6,649,876 B2
(45) Date of Patent: Nov. 18, 2003

(54) METHODS AND APPARATUSES FOR AUTOMATIC PROCESS CONTROL FOR FIRING AND BIASING HEATED ELECTRODE REFRIGERANT SENSORS

(75) Inventor: Dennis Cardinale, Plantation, FL (US)

(73) Assignee: Advanced Test Products, Inc., Miramar, FL (US)

( * ) Notice: Subject to any disclaimer, the term of this patent is extended or adjusted under 35 U.S.C. 154(b) by 102 days.

(21) Appl. No.: 10/086,188

(22) Filed: Feb. 28, 2002

(65) Prior Publication Data

US 2002/0157237 A1 Oct. 31, 2002

Related U.S. Application Data

(63) Continuation-in-part of application No. 09/838,169, filed on Apr. 19, 2001.
(60) Provisional application No. 60/297,932, filed on Jun. 13, 2001.

(51) Int. Cl.[7] .......................... G01L 27/04; H05B 3/02; H05B 3/06; H01L 21/48; G01N 3/62
(52) U.S. Cl. ..................... 219/385; 219/209; 204/431; 73/31.05; 73/25.05
(58) Field of Search .............................. 219/385, 200, 219/201, 209; 204/431; 73/25.01, 25.05, 31.05, 40.7

(56) References Cited

U.S. PATENT DOCUMENTS

| | | | |
|---|---|---|---|
| 3,739,260 A | 6/1973 | Schadler ..................... 324/33 |
| 3,751,968 A | * 8/1973 | Loh et al. .................. 73/31.05 |
| 3,912,967 A | 10/1975 | Longenecker ............... 315/107 |
| 3,991,360 A | 11/1976 | Orth et al. ..................... 324/33 |
| 4,151,641 A | 5/1979 | Mitoff ........................... 29/611 |
| 4,157,311 A | 6/1979 | Orth et al. ................... 252/408 |
| 4,171,341 A | 10/1979 | Morgan ......................... 422/98 |
| 4,203,199 A | 5/1980 | Morgan ......................... 29/612 |
| 4,305,724 A | 12/1981 | Micko ........................... 23/232 |
| 4,609,875 A | 9/1986 | Jeffers ......................... 324/455 |
| 4,879,546 A | 11/1989 | Dunham et al. ............. 340/632 |
| 4,910,463 A | 3/1990 | Williams, II et al. ........ 324/468 |
| 5,104,513 A | 4/1992 | Lee et al. .................... 204/425 |
| 5,198,774 A | 3/1993 | Williams, II et al. ........ 324/468 |
| 5,226,309 A | 7/1993 | Stetter et al. .............. 73/31.06 |
| 5,284,569 A | 2/1994 | Lee et al. .................... 204/425 |
| 5,351,037 A | 9/1994 | Martell et al. ............... 340/632 |
| 5,400,015 A | 3/1995 | Liebermann ................. 340/632 |
| 5,444,435 A | 8/1995 | Williams, II et al. ........ 340/632 |
| 5,448,905 A | 9/1995 | Stetter et al. .............. 73/31.05 |
| 5,490,413 A | 2/1996 | Atkinson ....................... 73/40 |
| 5,608,384 A | 3/1997 | Tikijian ....................... 340/632 |
| 5,841,021 A | 11/1998 | De Castro et al. ........... 73/23.2 |
| 5,932,176 A | 8/1999 | Yannopoulos et al. ........ 422/98 |
| 6,085,576 A | 7/2000 | Sunshine et al. .......... 73/29.01 |

OTHER PUBLICATIONS

D-TEK Refrigerant Leak Detector User's Manual, Leybold Inficon, (19 pages).

(List continued on next page.)

Primary Examiner—Joseph Pelham
(74) Attorney, Agent, or Firm—Baker & Hostetler LLP

(57) ABSTRACT

Methods and apparatuses are disclosed for automatic process control of firing and biasing a heated-electrode refrigerant sensor for use in a refrigerant detector. An unfired sensor may be mounted in a manufacturing station, and while remaining mounted may be electrically heated by applying current and adjustably controlling the amount of power to gradually increase the temperature. Once the sensor reaches a suitable temperature, the sensor is fired, and while the temperature of the sensor is elevated, the sensor is biased. The temperature increase may take place at a first rate until substantially all the moisture is removed, and then at a second rate. Upon reaching the bias temperature, the temperature may be held generally constant for a first period of time before increasing to a second bias temperature for a second period of time.

66 Claims, 5 Drawing Sheets

OTHER PUBLICATIONS

D–TEK Refrigerant Leak Detector User Guide, Leybold Inficon, (19 pages).

Top Gun™, H10Xpro Refrigeraent Leak Detector Operation Manual, Yokogawa Corporation of America.

Bacharach® The Informant™ Refrigerant Leak Detector Instruction 19–9210 Operation & Maintenance, Rev. 4—Apr. 2001.

* cited by examiner

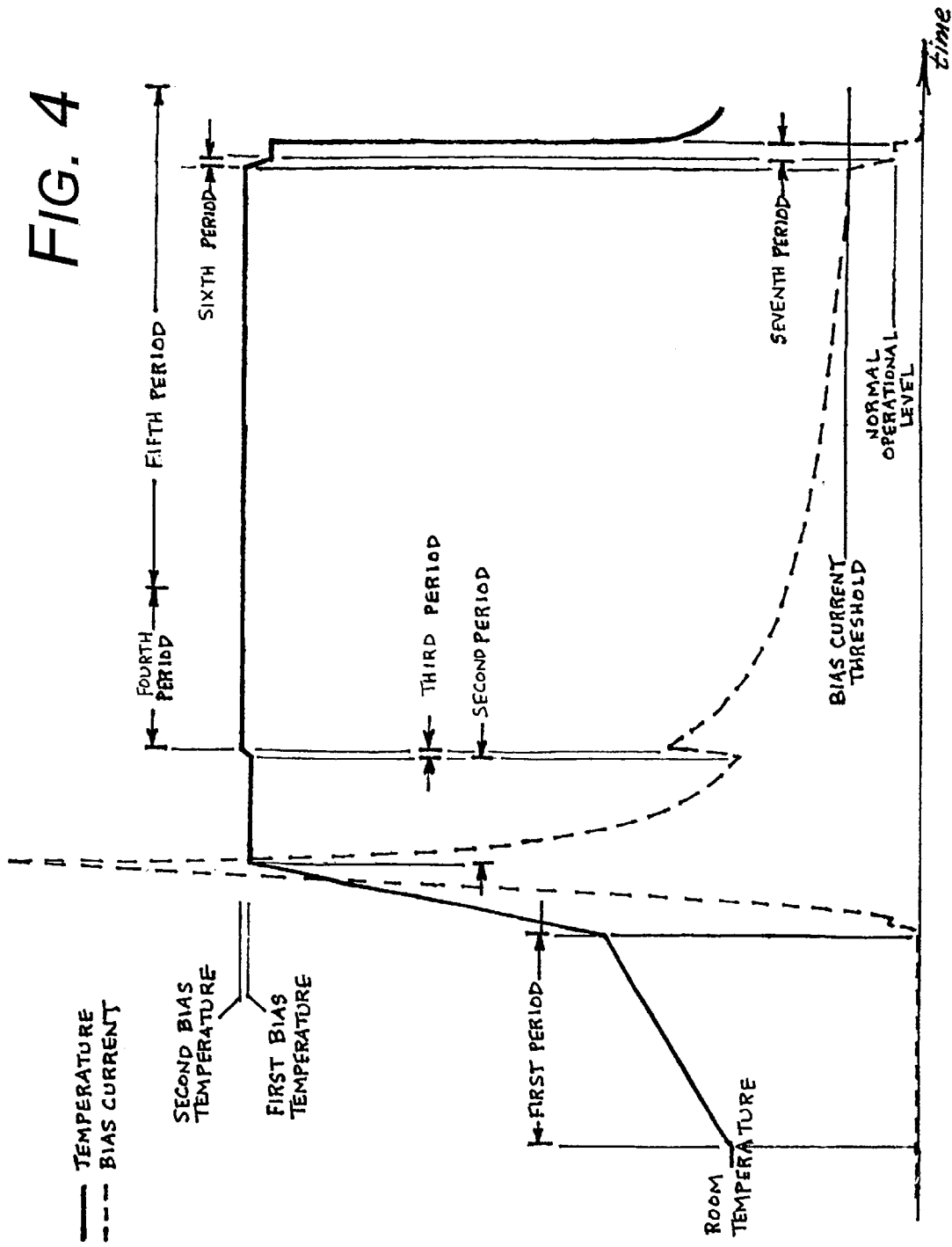

METHODS AND APPARATUSES FOR AUTOMATIC PROCESS CONTROL FOR FIRING AND BIASING HEATED ELECTRODE REFRIGERANT SENSORS

CROSS-REFERENCE TO RELATED APPLICATIONS

This application is a continuation-in-part, and claims the benefit of, non-provisional U.S. patent application Ser. No. 09/838,169, filed Apr. 19, 2001, entitled "HEATED ELECTRODE REFRIGERANT DETECTOR UTILIZING ONE OR MORE CONTROL LOOP." In addition, this application is entitled to the benefit of, and claims priority to, U.S. Provisional Patent Application Ser. No. 60/297,932, filed Jun. 13, 2001, entitled "AUTOMATIC PREPARATION AND PROCESS CONTROL FOR HEATED ELECTRODE REFRIGERANT SENSORS." The entirety of each of these patent applications is incorporated herein by reference.

BACKGROUND OF THE PRESENT INVENTION

1. Field of the Present Invention

The present invention relates generally to the field of gas detectors, and, in particular, to the art of more efficiently firing, biasing and testing "heated electrode" halogenated refrigerant sensors using control theory to control the operation of the detector using an advanced sensing device and one or more control loops.

2. Background Art

The need for a reliable method or apparatus for detecting leaks from refrigerant systems has long been well known. A number of leak detectors have been developed to meet this need. One well known type of leak detector makes use of a "heated electrode" sensing device to indicate the presence of trace quantities of halogenated refrigerants. Such sensors are generally constructed of a platinum anode/heater coil and a platinum cathode wire within the coil, and are coated with a ceramic slurry consisting of alumina and a silicate of an alkali metal such as sodium, potassium, or rubidium. The ceramic forms an electrically resistive layer between the electrodes. When heated by an electrical current passing through a first of the electrodes, an outer layer depleted of ions develops along the electrodes. When this layer is exposed to reactive gases like halogen, ions flow across the depletion zone and the conductivity of the device is increased. Thus, the presence of halogenated gases may be indicated by monitoring the current generated through the second electrode, referred to as the bias current, for a sudden increase in magnitude created by introducing the device to such gases. These sensors are commonly utilized by technicians to determine whether a refrigerant leak exists and to pinpoint its source.

For such a device to function reliably as a refrigerant sensor, the assembly must be fired (to sinter the ceramic), and also "biased" to create the ion depletion region across which ions flow in the presence of refrigerant. Typically, the firing and the biasing operations are performed separately. The firing operation takes place in a kiln at a high temperature and requires a relatively lengthy period of time. Subsequently, the fired assembly is mounted in its holder, which may be a TO-5 transistor can, and current is passed through the anode coil to heat the sensor while a bias voltage is applied between the anode coil and cathode wire. Over another relatively lengthy period of time, the depletion region is formed.

Unfortunately, prior art systems and methods have a number of significant drawbacks. First, the firing operation typically requires 3 or more hours, and the biasing operation requires up to 12 more hours, and thus collectively consume a very large amount of manufacturing time before the sensor testing for compliance to specifications may even begin. Also, the holder, such as the TO-5 transistor can, typically cannot withstand the high firing temperatures to which it must be subjected in the kiln, and thus the anode/cathode assembly must be fired separately and attached to the can afterwards, prior to biasing. Therefore, significant time and labor may have already transpired without any knowledge as to the ultimate performance (or lack there of) of the final sensor. Further, the sensor must be completely tested under operating conditions, rather than during or immediately after the biasing process, to ensure compliance to specifications, because variations in the ceramic mixture and in the construction of the sensor may have significant impact upon the final operation of that particular sensor. Finally, since the construction and the firing, biasing and testing operations require so much time, the operations must occur in large batches such that production throughput is optimized. Variations in the process could potentially produce hundreds or thousands of failures, resulting in a great deal of waste material and lost time, in addition to the time required to bring the processes back into specification.

Alternatively, some sensors are fired by passing a current through the coil to obtain temperatures sufficient to sinter the sensor. Biasing may also be accomplished by maintaining the elevated temperatures for an extended period of time. However, existing electrical heating methods involve only the crude application of a sufficient amount of heat to sinter and bias, without regard to how the temperature is raised to such temperatures, thus raising the risk of damage to the sensor during the process. No consideration is given to the amount of moisture present in the sensor as the temperature is increased. Further, such methods do not take into consideration any information about the state of the sensors being fired or biased while the heating is taking place, and thus result in significant inefficiencies in the amount of time required for the manufacture of sensors.

Thus, a need exists for an improved method of manufacturing heated electrode refrigerant sensing devices.

SUMMARY OF THE PRESENT INVENTION

Briefly summarized, the present invention relates to methods and apparatuses for automatically controlling the processes of firing and biasing heated electrode refrigerant sensors for use in refrigerant leak detectors in general. Broadly defined, the present invention according to one aspect includes a method of, and apparatuses for, manufacturing a heated-electrode refrigerant sensor for use in a refrigerant detector, wherein the method includes the steps of: mounting an unfired sensor in a manufacturing station; and, while the unfired sensor remains mounted in the manufacturing station, electrically heating the sensor by applying current to the sensor, adjustably controlling the amount of power applied to the sensor to gradually increase the temperature of the sensor over a period of time, firing the sensor once the sensor reaches a suitable temperature, and, while the temperature of the sensor is elevated, biasing the sensor.

In features of this aspect, the period of time is between 4 and 30 minutes; the rate of temperature increase does not exceed 500 degrees Celsius per minute; a substantial portion of the temperature increase occurs at a generally constant rate of between 10 and 50 degrees Celsius per minute; the method further includes the step of monitoring the temperature of the sensor and the step of adjustably controlling the applied power includes adjustably controlling the applied power on the basis of the monitored temperature; the method further includes the step of providing, prior to the step of mounting, an unfired sensor having an anode/cathode assembly and a housing; the method further includes the step of attaching the housing to the anode/cathode assembly prior to mounting the unfired sensor in the manufacturing station; the steps of controlling the current to gradually increase the temperature, firing the sensor, and biasing the sensor are cumulatively completed in less than 2 hours; and the step of firing the sensor begins while the temperature is still being increased.

The present invention according to another aspect includes a method of, and apparatuses for, manufacturing a heated-electrode refrigerant sensor for use in a refrigerant detector, wherein the method includes the steps of: generating a bias current in the sensor; gradually raising the temperature of the sensor at a first rate of increase; and after substantially all moisture has been removed from the sensor, gradually raising the temperature of the sensor at a second rate of increase.

In features of this aspect, the second rate of increase is greater than the first rate of increase; the method further includes the step of determining, while raising the temperature at the first rate of increase, that substantially all moisture has been removed from the sensor; the step of determining includes monitoring the magnitude of the bias current; the step of monitoring includes detecting the substantial absence of a bias current; the step of raising the temperature of the sensor at a second rate of increase is conditional upon a determination that substantially all moisture has been removed from the sensor; the first rate of increase is between 10 and 50 degrees Celsius per minute; the second rate of increase is between 50 and 500 degrees Celsius per minute; the step of raising the temperature at a second rate of increase is initiated at a predetermined time which is between 2 and 20 minutes after the initiation of the step of raising the temperature of the sensor at the first rate of increase; the method further includes the step of biasing the sensor, after raising the temperature at a second rate of increase, by maintaining the temperature of the sensor at or above a predetermined temperature until the predetermined temperature is reached; the biasing step includes maintaining the temperature of the sensor substantially constant at the predetermined temperature for the predetermined period of time; and the method further includes firing the sensor upon reaching a suitable temperature which is reached during the gradual temperature increase at the second rate.

The present invention according to yet another aspect includes a method of, and apparatuses for, manufacturing a heated-electrode refrigerant sensor for use in a refrigerant detector, wherein the method includes the steps of: generating a bias current in the sensor; gradually increasing the temperature of the sensor from an initial temperature to a first bias temperature; upon reaching the first bias temperature, biasing the sensor by holding the temperature of the sensor generally constant for a first period of time; after the expiration of the first period of time, increasing the temperature of the sensor to a second bias temperature; and upon reaching the second bias temperature, further biasing the sensor by holding the temperature of the sensor generally constant for a second period of time.

In features of this aspect, the method further includes monitoring the bias current while the temperature is held substantially constant for the second period of time; the difference between the first and second bias temperatures is less than 50 degrees Celsius; the first period of time is predefined to be less than 6 minutes; the second period of time is predefined to be between 8 and 30 minutes; the length of the second period of time is determined on the basis of a sensor operating condition; the sensor operating condition is the magnitude of the bias current; and the variance of the sensor temperature during the first period of time and the variance of the sensor during the second period of time are each less than 5 degrees Celsius.

BRIEF DESCRIPTION OF THE DRAWINGS

Further features, embodiments, and advantages of the present invention will become apparent from the following detailed description with reference to the drawings, wherein:

FIG. 4 is a graphical illustration of an example of the respective magnitudes of the temperature of the sensor and the bias current of the sensor during the burn/bias/test process carried out by the manufacturing station of FIG. 1.

DETAILED DESCRIPTION OF THE PREFERRED EMBODIMENTS

Figure 1:
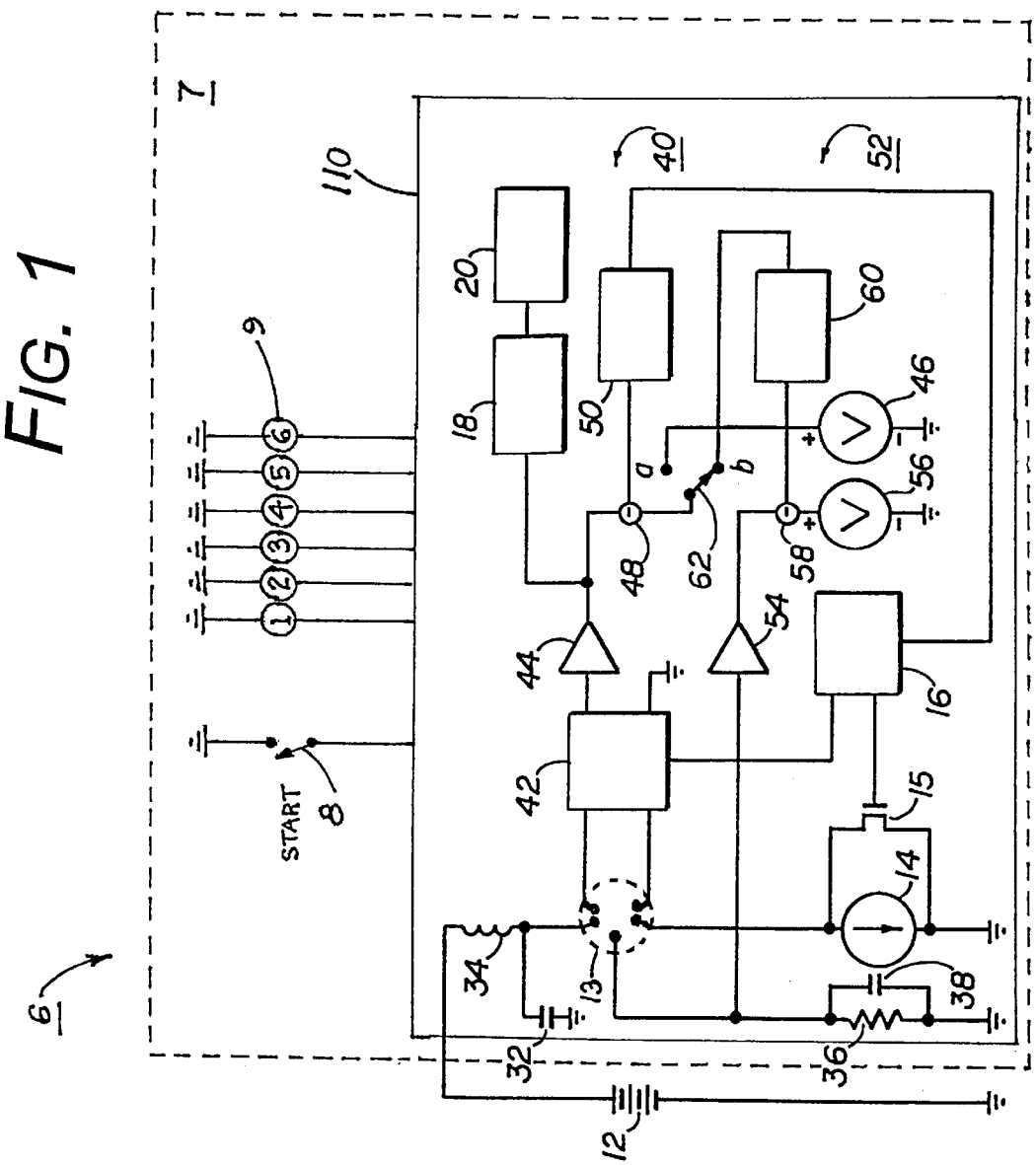
FIG. 1 is a schematic diagram of a manufacturing station in accordance with the preferred embodiments of the present invention.

FIG. 1 is a schematic diagram of a manufacturing station 6 in accordance with the preferred embodiments of the present invention. The manufacturing station 6 includes one or more manufacturing units for simultaneously preparing one or more refrigerant sensors 111 for use in a refrigerant detector. Many of the components shown in FIG. 1 are similar to, and bear the same reference numerals, as those in the above-referenced non-provisional patent application. The manufacturing station 6, sometimes referred to herein as a "burn fixture," includes a 5–6 volt power supply 12, one or more test sockets 13, and one or more printed circuit boards ("PCB") 7. In one preferred embodiment, each PCB corresponds to exactly one of the test sockets 13, and together each PCB and test socket combination forms a manufacturing unit which can fire, bias, and test one sensor 111 according to a predetermined process 300. Each PCB and test socket combination also has a "start" button 8 and a plurality of LED indicators 9, preferably including at least six, providing visual indication of the progress of the sensor 111 in the socket 13, as well as indication of the failure or success of the sensor 111. However, it should be obvious that the PCB's may be combined onto a smaller number of PCB's without departing from the scope of the present invention, in which case a single "start" button or varying combinations of LED indicators may instead be used.

Each PCB 7 provides all necessary circuitry 110 to continuously and automatically control and monitor multiple process variables, including time, power, temperature, and bias current, for a refrigerant sensing device (not shown). The circuitry 110 preferably includes a microprocessor (not specifically shown), a post-processor 18, an alarm 20 and two switchable control loops 40, 52 for controlling the temperature and the bias current, respectively, of the sensing device. In addition, one preferred embodiment of the circuitry 110 includes a current source 14, a switch 15 for bypassing the current source 14, a modulator 16 for modulating the switch 15 under control of the control loops 40, 52, and basic circuitry components such as a first and a second capacitor 32, 38, a resistor 36 and an inductor 34. In the preferred embodiment shown in FIG. 1, the control loops 40, 52 include a voltage potential converter 42, first and second gain amplifiers 44, 54, a temperature input means 46, a bias current input means 56, first and second subtractors 48, 58, first and second processing means 50, 60, and a controllable switch 62.

Circuitry 110 suitable for use with the present invention is disclosed in the commonly-assigned U.S. patent application Ser. No. 09/838,169, filed Apr. 19, 2001 and entitled "Heated Electrode Refrigerant Detector Utilizing One or More Control Loop" ("the '169 application"), the entirety of which is incorporated herein by reference. The circuitry 110 is preferably implemented via a microprocessor (not shown) and operated via suitable firmware for implementing the fire/bias/test process 300. It should be noted, however, that although the circuitry 110 may thus be the same or similar to that of the '169 patent application, the firmware may provide different functionality than any firmware utilized in the '169 patent application.

The present invention is generally utilized with refrigerant sensors of the well-known "heated electrode" type. As described in the '169 application, many of the principles of the circuitry 110 may be applied to heated electrode sensors of both the three-contact sensors and five-contact sensors. Because improved performance is generally provided by the five-contact ("Kelvin Connections") type, the following description will include only this type. However, it will be obvious that most or all of the present invention has equal applicability to either type of sensor.

Figure 2:
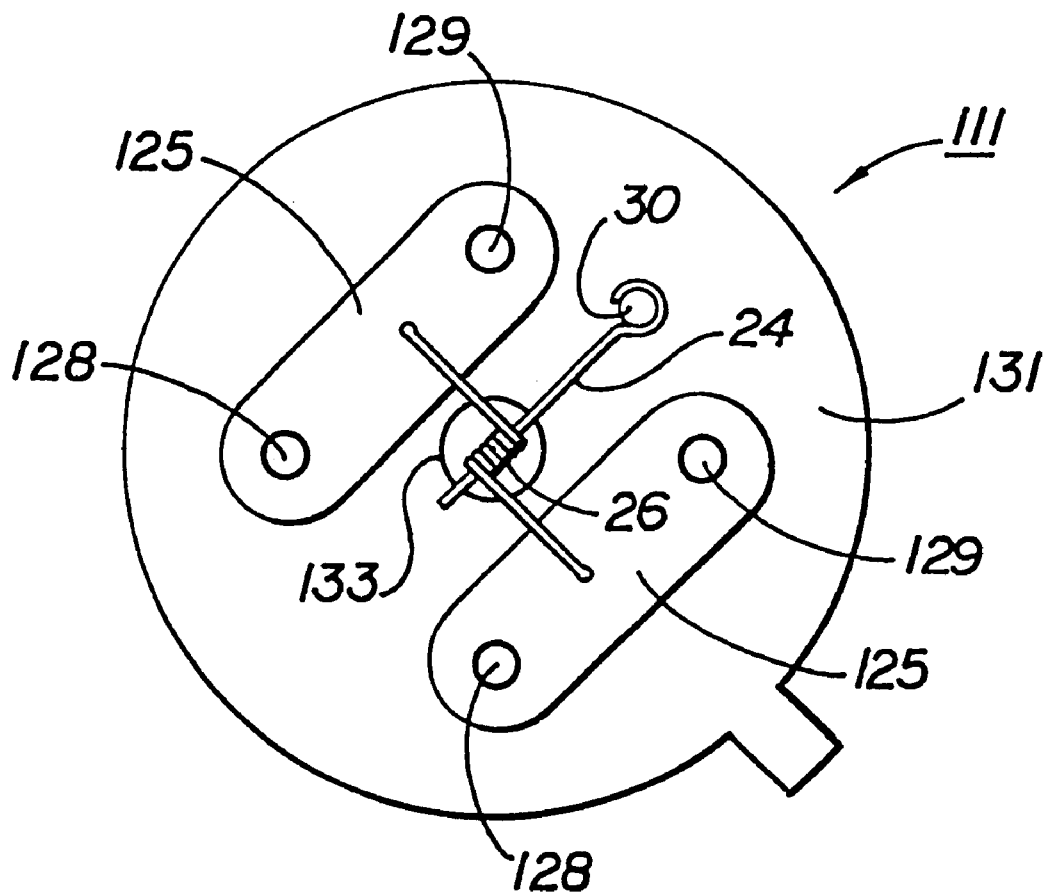
FIG. 2 is a detailed diagrammatic view of a sensor suitable for use with the manufacturing station of FIG. 1.

FIG. 2 is a detailed diagrammatic view of a sensor suitable for use with the manufacturing station 6 of FIG. 1. As per the '169 patent application, a sensor 111 suitable for use with the described methods includes an anode coil 26, a cathode wire 24, a header, and a housing (not shown). Such a sensor 111 may be constructed according to the following steps. First, an anode coil 26 may be created by winding a length of platinum wire. In a preferred embodiment, the anode coil 26 has five turns. A cathode wire 24 is then inserted into the anode coil 26 and the anode 26 and cathode 24 are fixed in place relative to each other. Next, the anode/cathode combination is coated with one or more coats of a ceramic slurry, which preferably contains alumina and a silicate of rubidium and/or other alkali metals. Each coat is allowed to air dry for a few minutes prior to application of the next coat.

After all the coats have been applied and the coated assembly is allowed to dry for a short period of time, the anode/cathode assembly is mounted onto the header, which includes a base 131 and a plurality of contacts 128, 129, 30 extending therethrough, such that the anode/cathode assembly is disposed adjacent to an air exhaust hole 133. Each end of the anode coil 26 is affixed to a bus bar 125 whose ends are connected to a respective supply or drive contact 128 and a temperature sense or Kelvin contact 129, and the cathode is connected to a cathode contact 30. The housing may then be affixed over the top of the header. In a preferred embodiment, the housing and header are a TO-5 transistor can welded onto a five-pin TO-5 transistor header. However, it should be obvious to one of ordinary skill that the teachings of the present invention may be equally applied to a variety of sensors utilizing other components and other construction methods without departing from the scope of the present invention.

Because errors may occur during the manufacturing process that will result in non-conforming sensors 111, it is critical to be able to identify such sensors and to do so as early in the process as possible. Such errors may include, but are not limited to, the following: too few or too many turns on the sensor's anode coil 26; the sensor's anode coil 26 being wound too tight, resulting in shorted coils; the sensor's cathode wire 24 being shorted to its anode coil 26; too little or too much ceramic slurry being present on the anode/cathode assembly; the ceramic slurry being too viscous or not viscous enough; and the like. In addition, during the firing or biasing of the sensor 111, the anode coil 26 could encounter an "open" or "shorted" condition, the cathode wire 24 could short to the anode wire 26, or the connections between the electrodes 24, 26 and the pins of the can could become detached. Further, a sensor 111 that successfully completes the fire/bias operation may exhibit unusually high noise or adverse electrical properties.

Figure 3A:
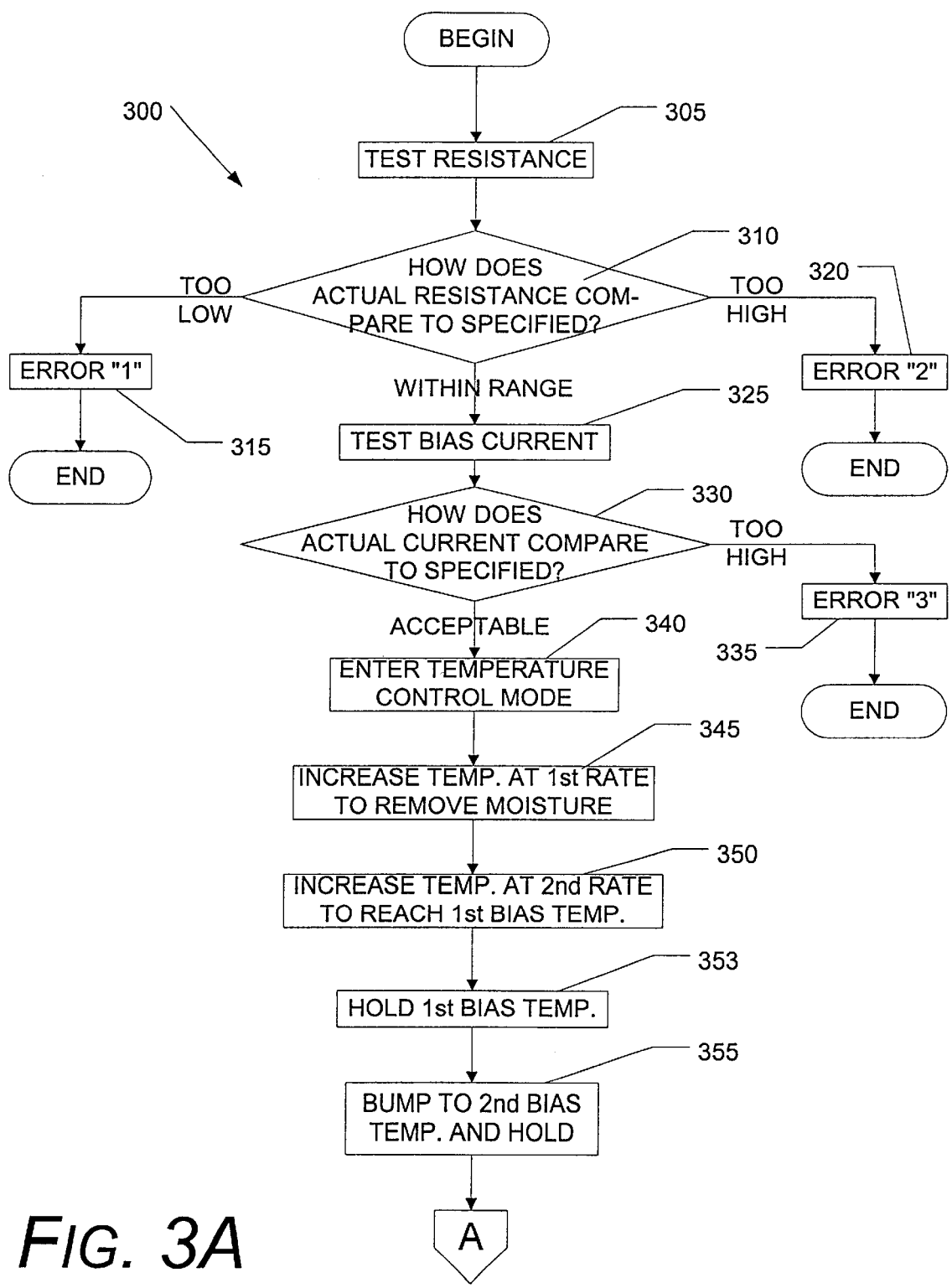
FIGS. 3A and 3B are a flowchart representation of a burn/bias/test process carried out by the manufacturing station of FIG. 1.
Figure 3B:
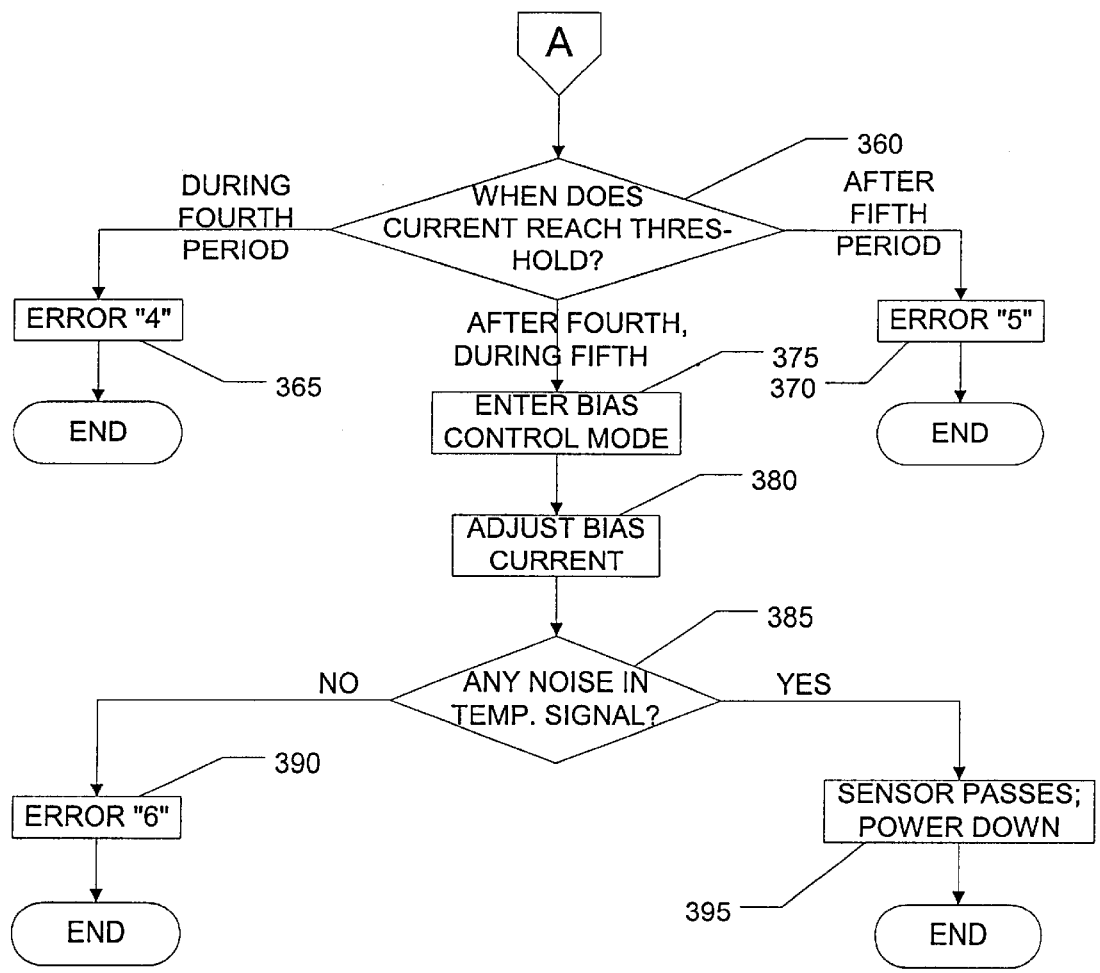

FIGS. 3A and 3B are a flowchart representation of the burn/bias/test process 300 carried out by the manufacturing station 6 of FIG. 1. As described in detail hereinbelow, this process 300 may be used to identify a variety of problems with the sensors during the steps of firing, biasing and testing the sensors 111. When a failure is detected, a "reason" code may be displayed or provided such that the failure information can be fed back to the beginning of the assembly line so as to make rapid corrections to the sensor construction process. The operation of the burn/bias test process 300 and its relationship to the overall manufacturing process is described next.

Once a sensor 111 has been assembled and visually checked for obvious problems, the newly-fabricated sensor 111 is inserted into one of the sockets 13 of the burn fixture 6. The burn/bias/test process 300 illustrated in FIGS. 3A and 3B is then initiated by the depression of the "start" button 8, and the following steps are carried out under the control of the firmware. First, at step 305, the resistance of the sensor 111 is tested, and at step 310 the measured resistance is compared to a predetermined range of values. If the measured resistance falls below a predetermined minimum value, then a shorted anode 26 or an anode coil 26 having an insufficient number of turns is indicated, and the sensor 111 is rejected with error "1" at step 315 and the process 300 is terminated. On the other hand, if the measured resistance exceeds a predetermined maximum value, then an "open" or disconnected anode 26 or an anode coil 26 having an excessive number of turns is indicated, and the sensor 111 is rejected with error "2" at step 320 and the process 300 is terminated.

If at step 310 the measured resistance of the resistor 111 is within the predetermined range, then at step 325 the firmware proceeds to use the fixture 6 to measure the bias current, and at step 330 the measured bias current is compared to a predetermined maximum value. If the bias current exceeds the predetermined maximum, then a short between the cathode 24 and the anode 26 is indicated, and the sensor 111 is rejected with error "3" at step 335 and the process 300 is terminated.

If at step 330 the measured bias current is less than the predetermined maximum, then the manufacturing step of firing the sensor 111 is begun. Firing generally includes the process of raising the temperature of the sensor to a level sufficient to enable sintering to occur. Firing begins at step 340 as the firmware causes the circuitry 110 to enter temperature control mode as described in the '169 application. The initial temperature of the sensor 111 at this point will typically be the ambient temperature of the sensor's surroundings. Starting from this point, at step 345 the temperature control loop 40 of the circuitry 110 is used to slowly raise the temperature of the sensor 111 at a first predetermined rate of temperature increase. This is accomplished by slowly adjusting the power which is supplied to the sensor 111 as more fully described in the '169 application. During this stage, all residual moisture is removed from the sensor 111. The rate of temperature increase is selected to be as high as possible in order to minimize the amount of time required to remove substantially all of the moisture but not so high as would unreasonably raise the risk of cracking or otherwise damaging the ceramic during the process 300. The first temperature increase rate preferably lies within a range of about 10 to about 50 degrees Celsius ("° C.") per minute, with a most preferred increase rate of about 28° C. per minute.

This increase may be continued for a first predetermined period of time or until a first predetermined temperature is reached, as desired, with a respective value for either being selected calculated as that which is sufficient to ensure that substantially all moisture is eliminated from the ceramic at the chosen rate of temperature increase. The first predetermined period of time preferably lies within a range of about 2 to about 20 minutes, or a first predetermined temperature preferably lies within a range of about 150° C. to 500° C. At the most preferred warming rate of 28° C. per minute, a first predetermined period of time suitable for use with a preferred embodiment of the present invention is approximately ten minutes, or a first predetermined temperature is approximately 300° C. However, it should be clear that other periods, temperatures and rates of temperature increase may alternatively be selected based on the amount of moisture likely to be present, on the amount of time likely to be required to remove a suitable amount of the moisture, and the like. Alternatively, the amount of remaining moisture may be periodically measured and the temperature increase may be halted once the measured moisture drops to zero. Because a current is generated when moisture is present, the presence of moisture in the sensor 111 may be reliably indicated by the presence of a bias current, and the amount of moisture may be indicated by the magnitude of such a current.

Next, at step 350, the sensor temperature is further raised at a second rate of increase while the bias voltage is continuously applied until a second predetermined temperature is reached. Once a sufficient temperature level is reached, either during step 345 or 350, the sintering process begins, during which the ceramic is slowly solidified. As the temperature is raised, water created during crystallization is slowly burned from the ceramic so that "cementing" of the sensor 111 during sintering is prevented. Because substantially all of the previous moisture in the sensor 111 has been removed, the second rate of increase may be greater than the first, thus helping to minimize the overall time required for the process 300. A second predetermined temperature, sometimes referred to herein as the first bias temperature, which is suitable for use with the present invention is 1000° C. The second temperature increase rate is preferably constant and lies within a range of about 50 to about 500° C. per minute, with a most preferred increase rate of about 233° C. per minute. However, it should be obvious that non-constant rates may be utilized without departing from the scope of the present invention. The first bias temperature may thus preferably be reached within 4 to 30 minutes after the temperature adjustment is begun, depending upon the moisture present in the sensor 111, the desired first bias temperature, the desired reliability of the process, and the like, with a most preferred time of approximately 13 minutes.

While the sensor 111 remains in the burn fixture 6 and the temperature of the sensor 111 remains elevated, the biasing process is preferably also initiated. In general, biasing involves heating a sensor being biased by passing an electrical current through the sensor's electrodes to develop an outer ion-depleted layer on each electrode. As is well known, when this layer is then exposed to reactive gases like halogen, ions flow across the depletion zone and the conductivity of the device is increased. Because electrically heating the sensor 111 is the mechanism by which both the biasing process and the firing process are carried out, and because the required temperatures for the two processes may be approximately the same, these processes may, and preferably do, occur at least partially simultaneously. Thus, the biasing process is preferably initiated by the time the sensor 111 reaches the first bias temperature, if not sooner. Meanwhile, at step 353, the temperature of the sensor 111 is preferably held generally constant at the first bias temperature for a second predetermined period of time. The second predetermined period of time is preferably less than about 30 minutes, and more preferably less than about six minutes, with an exemplary value of about five minutes. Because a significant amount of biasing is accomplished during the second predetermined period of time, the first bias temperature is chosen to help minimize the amount of time required to bias the sensor 111 while at the same time maximizing the reliability of the process. As described hereinabove, a first bias temperature suitable for use with the present invention is in the range 900° C. to 1100° C., and preferably 1000° C., but useful results may be obtained with temperatures ranging from 500° C. to 1500° C. The temperature control loop 40 permits the temperature of the sensor 111 to be precisely controlled, but it should be clear that less precise control systems may be used without departing from the scope of the present invention, and that variations in the temperature of up to 50° C. may be permitted.

Next, at step 355, the temperature may be increased again to a third predetermined temperature. This increase, the purpose of which is to accelerate the biasing process, occurs over a third predetermined period of time, which is preferably relatively short. As illustrated, the magnitude of the bias current increases sharply as a result of the temperature increase before descending again once the third predetermined temperature is reached. It should be clear that this "bump" in the temperature of the sensor 111 is not required, but is believed to reduce the amount of time required to reliably bias the sensor 111. A third predetermined temperature, sometimes referred to herein as the second bias temperature, which is suitable for use with the present invention is 1022° C., and a third predetermined period of time suitable for use with the present invention is 20 seconds. It should be clear that other values for both the first and second bias temperatures and for the third predetermined period of time may be selected without departing from the scope of the present invention. However, the difference between the first and second bias temperatures is preferably less than about 200° C., and more preferably less than about 50° C.

Meanwhile, once the sensor 111 has been at least partially biased, further electrical testing of the construction of the sensor may be initiated. Preferably, the electrical testing at least includes testing the construction of the sensor's ceramic coating. Important characteristics of the ceramic coating include the coating's chemical composition and the quantity of ceramic coating which has been applied to the sensor, the latter sometimes being referred to as the "thickness" of the sensor. Such testing may be achieved by monitoring the bias current to determine how quickly, after one of the bias temperatures is reached, the bias current drops to a threshold value. While monitoring the bias current, the sensor 111 is maintained at the bias temperature for a fourth predetermined period of time, and then, if necessary, for some or all of a fifth predetermined period of time. A sensor 111 is acceptable only if the bias current drops to the threshold value after the expiration of the fourth predetermined period of time but before the expiration of the fifth predetermined period of time. In the preferred embodiment, the bias current is monitored from the moment the sensor temperature reaches the second bias temperature rather than the first, but if no temperature "bump," such as the one carried out at step 355, is to be utilized, then the bias current may instead be monitored from the moment the sensor temperature reaches the first bias temperature.

The ceramic construction test is illustrated in the flowchart of the process 300 beginning at step 360. If the bias current drops below the threshold value during the fourth predetermined period of time, the sensor 111 is rejected with error "4" at step 365, indicating either that the coating of ceramic on the sensor 111 is too thin or that the chemical composition of the ceramic is correspondingly imbalanced, and the process 300 is terminated. Alternatively, if at step 360 the bias current not only fails to drop below the threshold value during the fourth predetermined period of time but also during the fifth predetermined period of time, the sensor 111 is rejected with error "5" at step 370, indicating that the coating of ceramic on the sensor 111 is too thick or that the chemical composition of the ceramic is correspondingly imbalanced, and the process 300 is terminated. A failure of this type (i.e., either error "4" or error "5") would indicate either that the proportions of the rubidium silicate, alumina, or the like in the ceramic slurry are incorrect or that an incorrect quantity of slurry has been applied.

A fourth predetermined period of time suitable for use with the present invention is in the range of 360 to 600 seconds, and preferably 490 seconds, and a fifth predetermined period of time suitable for use with the present invention is in the range of 900 to 3600 seconds, and preferably 1310 seconds. However, useful results may be obtained with a fourth predetermined period of time ranging from 30 to 1800 seconds, and with a fifth predetermined period of time ranging from 300 to 7200 seconds. The threshold value may be predetermined, or may be calculated according to any measured or derived parameters, such as time, power, temperature, current, or the like. If a predetermined threshold value is to be used, a threshold value suitable for use with the present invention is 1.35 $\mu$A. The total duration for which the sensor 111 remains at the second bias temperature preferably lies within a range of about 5 minutes to about 2 hours, with a more preferable duration of between 15 minutes and 1 hour.

Preferably, electrical testing of the construction of the sensor also includes monitoring an output signal of the sensor 111 for noise. If the electrical testing includes both testing the construction of the sensor's ceramic coating and monitoring an output signal for noise, then the noise test preferably follows immediately after the ceramic construction test. In that case, if at step 360 the construction of the ceramic is acceptable (i.e., if the bias current successfully drops to the threshold value after the expiration of the fourth predetermined period but before the end of the fifth predetermined period), then at step 375 the firmware next sets the circuitry 110 to operate in bias control mode, and at step 380 the bias current set point is adjusted to a predetermined normal operational level over a sixth predetermined period of time. A sixth predetermined period of time suitable for use with the present invention is 20 seconds, and a normal operational level suitable for use with the present invention is 0.4 $\mu$A.

In this regard, it should be noted that it is not strictly necessary to remain in temperature control mode or to maintain the temperature of the sensor 111 at the second bias temperature if the bias current threshold value is reached after the beginning but before the end of the fifth predetermined period Instead, the fifth predetermined period may be curtailed and the circuitry 110 may be set to operate in bias control mode as soon as the threshold value is reached. Also, it should be noted that the length of the sixth predetermined period is variable. The chosen period of time should be selected to enable the predetermined normal operational level to be reached quickly without creating too sharp a temperature step while adjusting the current.

Next, at step 385, the temperature signal is monitored for noise for a seventh predetermined period of time. The presence, magnitude, duration and other characteristics of noise on a signal may be detected or determined in a variety of well known ways using hardware and/or software means which would be obvious to one of ordinary skill in the art, and it should be clear that the amount of noise which is acceptable on such a signal may be predefined by the manufacturer based on reliability, yield, and other known characteristics. If noise, or an excessive amount thereof, is detected during the seventh predetermined period, then the sensor 111 is rejected at step 390 with error "6", indicating that the sensor 111 is too noisy, and the process 300 is terminated. A seventh predetermined period of time suitable for use with the present invention is 40 seconds. On the other hand, if at step 385 no noise, or only an acceptable quantity thereof, is detected during the seventh predetermined period of time, then at step 395, the firmware turns off the sensor 111 and signals the operator that the sensor 111 is ready for use and that the operation is complete.

Either of the two electrical tests of the construction of the sensor 111 described above may be used with or without the other test. If only the ceramic construction test is used, then after the completion of step 360 the firmware would proceed directly to step 395 as described above. Alternatively, if only the noise test is used, then at least steps 360–370 may be omitted. Further, because the sensor 111 being tested remains in the socket 13 in the burn fixture 6 throughout the fire/bias/test process 300, the noise test may overlap with the biasing operation or even the sintering operation, as long as the bias current is controlled to effect a suitable biasing or sintering temperature for a suitable period of time.

While steps 345–395 are being executed, the anode voltage (indicative of temperature) and the cathode are both continuously monitored as described at steps 305–335. Any failure of the anode 26 (i.e. burning open, etc.) is immediately detected and indicated to the operator as a failure of error-type "1" or "2". Contact between the cathode 24 with the anode 26 is indicated by a sudden increase or "jump" in the cathode voltage, or if the cathode voltage goes "full scale". Such contact is likewise reported to the operator as a failure of error-type "3".

When a sensor 111 is rejected, the failure mode may be noted either automatically, by the microprocessor or a facility connected thereto, or manually, by an operator. This information, as well as any information that can be gleaned from visual inspection, additional electrical testing, and the like, may then optionally be immediately fed back to the sensor manufacturing processes, so that those processes may be adjusted to eliminate the failures in subsequently manufactured sensors.

FIG. 4 is a graphical illustration of an example of the respective magnitudes of the temperature of the sensor 111 and the bias current of the sensor 111 during the burn/bias/test process 300 carried out by the manufacturing station 6 of FIG. 1. As illustrated, once the circuitry 110 enters temperature control mode at step 340, the temperature is steadily raised at step 345 from its starting point at room temperature until substantially all of the residual moisture is removed from the sensor 111 over a first period of time, which may be predetermined. The temperature of the sensor 111 may then be increased at a faster rate at step 350 until the first bias temperature is reached. During this time, the bias current increases very rapidly. Once the first bias temperature is reached, this temperature is maintained at step 353 for a second period of time while the bias current begins to decrease. Meanwhile, once sufficient temperatures are reached, the sensor 111 is both sintered and biased, preferably at least partially simultaneously.

Next, at step 355, the temperature may be "bumped" slightly over a fourth period of time to a second bias temperature in order to accelerate the biasing process. This causes the bias current to increase rapidly again until the temperature levels off again at the second bias temperature, at which time the bias current begins to decrease once again. Meanwhile, at step 360, the circuitry 110 monitors the bias current during a fourth period and a fifth period to determine when the magnitude of the bias current reaches the predetermined threshold value. In the example shown, the bias current reaches the threshold value toward the end of the fifth period. It should also be noted that the threshold is approximately, but not exactly, equal to the asymptotic value of the magnitude of the bias current. This enables a maximum amount of biasing to occur in a minimum amount of time. However, it should be obvious that other thresholds may be chosen without departing from the scope of the present invention.

Because in the process example illustrated the threshold value is reached within the allotted period of time, the circuitry next enters bias control mode at step 375 and at step 380 the firmware adjusts the bias current to a normal operational level over a sixth period of time. The adjustment in the bias current and the corresponding drop in the temperature are both illustrated accordingly in FIG. 4. Once the normal operational level is reached, the temperature signal from the sensor 111 is then monitored for noise during a seventh period of time. During this period, the bias current is held steady at the normal operational level, and in the absence of any changes in the ambient conditions surrounding the sensor 111 and the manufacturing station 6, the temperature remains constant as well. Finally, at step 395, the sensor 111 is powered down, causing the bias current to return to zero and the temperature to return eventually to room temperature.

The above-described process 300 permits a sensor 111 to be fired, biased and tested in less than two hours, and preferably in less than one hour. This time period may be measured from the initiation of the temperature control mode at step 340 to the successful completion of the noise test at step 395.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method of manufacturing a heated-electrode refrigerant sensor for use in a refrigerant detector, comprising the steps of:

mounting an unfired sensor in a manufacturing station; and while the unfired sensor remains mounted in the manufacturing station:

electrically heating the sensor by applying current to the sensor;

adjustably controlling the amount of power applied to the sensor to gradually increase the temperature of the sensor over a period of time;

once the sensor reaches a suitable temperature, firing the sensor; and while the temperature of the sensor is elevated, biasing the sensor.

2. The method of claim 1, wherein the period of time is between 4 and 30 minutes.

3. The method of claim 2, wherein the rate of temperature increase does not exceed 500 degrees Celsius per minute.

4. The method of claim 3, wherein a substantial portion of the temperature increase occurs at a generally constant rate of between 10 and 500 degrees Celsius per minute.

5. The method of claim 4, wherein a substantial portion of the temperature increase occurs at a generally constant rate of between 10 and 50 degrees Celsius per minute.

6. The method of claim 2, further comprising the step of monitoring the temperature of the sensor, and wherein the step of adjustably controlling the applied power includes adjustably controlling the applied power on the basis of the monitored temperature.

7. The method of claim 2, further comprising the step of providing, prior to the step of mounting, an unfired sensor having an anode/cathode assembly and a housing.

8. The method of claim 7, further comprising the step of attaching the housing to the anode/cathode assembly prior to mounting the unfired sensor in the manufacturing station.

9. The method of claim 2, wherein the steps of controlling the current to gradually increase the temperature, firing the sensor, and biasing the sensor are cumulatively completed in less than 2 hours.

10. The method of claim 2, wherein the step of firing the sensor begins while the temperature is still being increased.

11. A manufacturing station for manufacturing a heated-electrode refrigerant sensor, comprising:

mounting means for supporting an unfired sensor;

means for electrically heating the sensor by applying current thereto while the sensor remains supported by the mounting means;

means for adjustably controlling the amount of power applied to the sensor to gradually increase the temperature of the sensor over a period of time while the sensor remains supported by the mounting means;

means for firing the sensor once the sensor reaches a suitable temperature while the sensor remains supported by the mounting means; and means for biasing the sensor while the temperature of the sensor is elevated and while the sensor remains supported by the mounting means.

12. The manufacturing station of claim 11, wherein the period of time is between 4 and 30 minutes.

13. The manufacturing station of claim 12, wherein the rate of temperature increase does not exceed 500 degrees Celsius per minute.

14. The manufacturing station of claim 13, wherein a substantial portion of the temperature increase occurs at a generally constant rate of between 10 and 500 degrees Celsius per minute.

15. The manufacturing station of claim 14, wherein a substantial portion of the temperature increase occurs at a generally constant rate of between 10 and 50 degrees Celsius per minute.

16. The manufacturing station of claim 12, further comprising means for monitoring the temperature of the sensor, and wherein the means for adjustably controlling the applied power includes means for adjustably controlling the applied power on the basis of the monitored temperature.

17. The manufacturing station of claim 12, wherein the unfired sensor supported by the mounting means has an anode/cathode assembly attached to a housing.

18. The manufacturing station of claim 12, wherein the means for firing the sensor begins the firing operation while the temperature is still being increased.

19. A manufacturing station for manufacturing a heated-electrode refrigerant sensor, comprising:

a socket for supporting an unfired sensor;

a current source for electrically heating the sensor by applying current thereto while the sensor remains supported by the socket;

a temperature controller for adjustably controlling the amount of power applied to the sensor to gradually increase the temperature of the sensor over a period of time while the sensor remains supported by the socket, whereby upon reaching a suitable temperature, the sensor is fired; and a voltage source for biasing the sensor while the temperature of the sensor is elevated and while the sensor remains supported by the socket.

20. The manufacturing station of claim 11, wherein the period of time is between 4 and 30 minutes.

21. The manufacturing station of claim 20, wherein the rate of temperature increase does not exceed 500 degrees Celsius per minute.

22. The manufacturing station of claim 21, wherein a substantial portion of the temperature increase occurs at a generally constant rate of between 10 and 500 degrees Celsius per minute.

23. The manufacturing station of claim 22, wherein a substantial portion of the temperature increase occurs at a generally constant rate of between 10 and 50 degrees Celsius per minute.

24. The manufacturing station of claim 20, further comprising a temperature monitor for monitoring the temperature of the sensor, and wherein the temperature controller includes a feedback loop for adjustably controlling the applied power on the basis of the monitored temperature.

25. The manufacturing station of claim 20, wherein the unfired sensor supported by the mounting means has an anode/cathode assembly attached to a housing.

26. A method of manufacturing a heated-electrode refrigerant sensor for use in a refrigerant detector, comprising the steps of:

generating a bias current in the sensor;

gradually raising the temperature of the sensor at a first rate of increase; and after substantially all moisture has been removed from the sensor, gradually raising the temperature of the sensor at a second rate of increase.

27. The method of claim 26, wherein the second rate of increase is greater than the first rate of increase.

28. The method of claim 27, further comprising the step of determining, while raising the temperature at the first rate of increase, that substantially all moisture has been removed from the sensor.

29. The method of claim 28, wherein the step of determining includes monitoring the magnitude of the bias current.

30. The method of claim 29, wherein the step of monitoring includes detecting the substantial absence of a bias current.

31. The method of claim 28, wherein the step of raising the temperature of the sensor at a second rate of increase is conditional upon a determination that substantially all moisture has been removed from the sensor.

32. The method of claim 27, wherein the first rate of increase is between 10 and 50 degrees Celsius per minute.

33. The method of claim 27, wherein the second rate of increase is between 50 and 500 degrees Celsius per minute.

34. The method of claim 27, wherein the step of raising the temperature at a second rate of increase is initiated at a predetermined time.

35. The method of claim 34, wherein the predetermined time is between 2 and 20 minutes after the initiation of the step of raising the temperature of the sensor at the first rate of increase.

36. The method of claim 27, further comprising the step of:

after raising the temperature at a second rate of increase, biasing the sensor by maintaining the temperature of the sensor at or above a predetermined temperature.

37. The method of claim 36, wherein the step of raising the temperature at the second rate continues until the predetermined temperature is reached.

38. The method of claim 36, wherein the biasing step includes maintaining the temperature of the sensor substantially constant at the predetermined temperature for the predetermined period of time.

39. The method of claim 27, further comprising the step of:

upon reaching a suitable temperature, firing the sensor.

40. The method of claim 39, wherein the suitable firing temperature is reached during the gradual temperature increase at the second rate.

41. A manufacturing station for manufacturing a heated-electrode refrigerant sensor for use in a refrigerant detector, comprising:

means for generating a bias current in the sensor;

means for gradually raising the temperature of the sensor alternatively at a first rate of increase or a second rate of increase; and means for causing the temperature raising means to shift from gradually raising the temperature of the sensor at the first rate of increase to the second rate of increase after substantially all moisture has been removed from the sensor.

42. The manufacturing station of claim 41, wherein the second rate of increase is greater than the first rate of increase.

43. The manufacturing station of claim 42, further comprising means for determining, while raising the temperature at the first rate of increase, that substantially all moisture has been removed from the sensor.

44. The manufacturing station of claim 43, wherein the means for determining includes means for monitoring the magnitude of the bias current.

45. The manufacturing station of claim 44, wherein the means for monitoring includes means for detecting the substantial absence of a bias current.

46. The manufacturing station of claim 43, wherein operation of the means for causing the temperature raising means to shift to the second rate of increase is conditional upon a determination that substantially all moisture has been removed from the sensor.

47. The manufacturing station of claim 42, wherein the first rate of increase is between 10 and 50 degrees Celsius per minute.

48. The manufacturing station of claim 42, wherein the second rate of increase is between 50 and 500 degrees Celsius per minute.

49. The manufacturing station of claim 42, wherein the means for causing the temperature raising means to shift to the second rate of increase includes means for measuring a predetermined period of time.

50. The manufacturing station of claim 49, wherein the predetermined time is between 2 and 20 minutes after operation of the means for raising the temperature of the sensor at the first rate of increase is initiated.

51. The manufacturing station of claim 42, further comprising:
    means for biasing the sensor by maintaining the temperature of the sensor at or above a predetermined temperature after raising the temperature at the second rate of increase.

52. The manufacturing station of claim 51, wherein the means for biasing includes means for maintaining the temperature of the sensor substantially constant at the predetermined temperature for the predetermined period of time.

53. The manufacturing station of claim 42, further comprising:
    means for firing the sensor upon reaching a suitable temperature.

54. A manufacturing station for manufacturing a heated-electrode refrigerant sensor for use in a refrigerant detector, comprising:
    a current source and a voltage source for generating a bias current in the sensor;
    a temperature controller for gradually raising the temperature of the sensor alternatively at a first rate of increase or a second rate of increase; and
    a triggering device for causing the temperature controller to shift from gradually raising the temperature of the sensor at the first rate of increase to the second rate of increase after substantially all moisture has been removed from the sensor.

55. The manufacturing station of claim 54, wherein the second rate of increase is greater than the first rate of increase.

56. The manufacturing station of claim 55, further comprising a moisture sensor for determining, while raising the temperature at the first rate of increase, that substantially all moisture has been removed from the sensor.

57. The manufacturing station of claim 56, wherein the moisture sensor includes a bias current monitor for monitoring the magnitude of the bias current.

58. The manufacturing station of claim 57, wherein the moisture sensor includes a circuit for detecting the substantial absence of a bias current.

59. The manufacturing station of claim 56, wherein the triggering device is the moisture sensor.

60. The manufacturing station of claim 55, wherein the first rate of increase is between 10 and 50 degrees Celsius per minute.

61. The manufacturing station of claim 55, wherein the second rate of increase is between 50 and 500 degrees Celsius per minute.

62. The manufacturing station of claim 55, wherein the triggering device includes a clock for measuring a predetermined period of time.

63. The manufacturing station of claim 62, wherein the predetermined period of time is between 2 and 20 minutes after operation of the temperature controller begins raising the temperature of the sensor at the first rate of increase.

64. The manufacturing station of claim 55, further comprising:
    a temperate control loop for maintaining the temperature of the sensor at or above a predetermined temperature after raising the temperature at the second rate of increase in order to bias the sensor.

65. The manufacturing station of claim 64, wherein the temperature is raised at the second rate until the predetermined temperature is reached.

66. The manufacturing station of claim 64, wherein the temperature control loop includes means for maintaining the temperature of the sensor substantially constant at the predetermined temperature for the predetermined period of time.

* * * * *